US006747127B1

(12) United States Patent
McComsey et al.

(10) Patent No.: US 6,747,127 B1
(45) Date of Patent: Jun. 8, 2004

(54) SUBSTITUTED HETEROCYCLIC ACYL-TRIPEPTIDES USEFUL AS THROMBIN RECEPTOR MODULATORS

(75) Inventors: David F. McComsey, Warminster, PA (US); Bruce E. Maryanoff, Forest Grove, PA (US); Michael J. Hawkins, Ambler, PA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 09/565,715

(22) Filed: May 5, 2000

Related U.S. Application Data

(63) Continuation-in-part of application No. 09/444,327, filed on Nov. 19, 1999, now abandoned.
(60) Provisional application No. 60/112,313, filed on Dec. 14, 1998.

(51) Int. Cl.[7] .................................................. C07K 5/08
(52) U.S. Cl. ............................ 530/331; 514/18; 514/19
(58) Field of Search .............................. 514/18; 530/331

(56) References Cited

U.S. PATENT DOCUMENTS

| | | | |
|---|---|---|---|
| 4,314,936 A | 2/1982 | Yaron et al. | 530/331 |
| 5,391,705 A | 2/1995 | Neises et al. | 530/331 |
| 5,696,231 A | 12/1997 | Abelman et al. | 530/331 |
| 6,017,890 A | 1/2000 | Oekstra et al. | 514/19 |
| 6,069,232 A | 5/2000 | Malikayl et al. | 530/331 |

FOREIGN PATENT DOCUMENTS

| | | |
|---|---|---|
| EP | 0503203 A1 | 9/1992 |
| HU | 9201875 | 6/1992 |
| HU | 9901290 A | 11/1999 |
| WO | WO 92/04371 A1 | 3/1992 |
| WO | WO 99/42475 A1 | 8/1999 |

OTHER PUBLICATIONS

Malik, Asrar B., "Thrombin–Induced Endothelial Injury", Seminars In Thrombosis and Hemostasis, Vol 12, No. 3, 1986.
Ho–Sam Ahn, "Structure–Activity Relationships of Pyrroloquinazolines as Thrombin Receptor Antagonists", Bioorganic & Medicinal Chemistry Letters 9 (1999) 2073–2078.
Cindy L.A. Jones, "Responese of a human megakaryocytic cell line to thrombin: Increase in intracellular free calcium and mitogen release", Biochimica et Biophysica Acta, 1136 (1992) 272–282.
Hoekstra W. J. et al., "Thrombin Receptor (PAR–1) Antagonists. Heterocycle–based peptidomimetics of the SFLLR agonist motif", Bioorganic & Medical Chemistry Letters, GB, Oxford, vol. 8, No. 13, Jul. 7, 1998, pp. 1649–1654.

Bernatowicz E. A., "Development of potent thrombin receptor antagonist peptides", Journal of Medicinal Chemistry, vol. 39, 1996, pp. 4879–4887.
McComsey D. F. et al., "Heterocycle–peptide hybrid compounds. Aminotriazole–containing agonists of the thrombin receptor (PAR–1)", Bioorganic & Medicinal Chemistry Letters, GB, Oxford, vol. 9, No. 10, May 17, 1999, pp. 1423–1428.
B. K. Hwang et al., "Enzyme–Catalyzed Peptide Segment Condensation Using 5 (4H)—Oxazolones as Acyl Donors", J. Am. Chem Soc., vol. 115, No. 17, 1993, pp. 7912–7913.
"Thrombin–Induced Events in Non–Platelet Cells are Mediated by the Unique Proteolytic Mechanism Established for the Cloned Platelet Thrombin Receptor", David T. Hung, et al., The Journal of Cell Biology, vol. 116, No. 3, Feb. 1992, pp. 827–832.
Thrombin Receptor Activation Causes Rapid Neural Cell Rounding and Neurite Retraction Independent of Classic Second Messengers, Kees Jaiink et al., The Journal of Cell Biology, vol. 118, N0. 2, Jul. 1992, pp. 411–419.
"Thrombin–Induced Expression of Indothelial P–selectin and Intercellular Adhesion Moleculte–1: A Mechanism for Stabilizing Neutrophil Adhesion", Yaeuo Sugama et al., The Journal of Cell Biology, vol. 119, No. 4, Nov. 1992, pp. 935–944.
"Molecular Cloning of a Functional Thrombin Receptor Reveals a Novel Proteolytic Mechanism of Receptor Activation", Thien–khal H. Vu et al., Cell, vol. 64, Mar. 1991, pp. 1067–1068.
"Thrombin Effects on Osteoblastic Cells–IL Structure––Function Relationships" Dimitris N. Tatakis et al., Biochemical and Biophysical Research Communications, vol. 174, No. 1, Jan. 1991, pp. 181–186.
"Thrombin Induces Release of Platelet–Derived Growth Factor–Like Molecule(s) by Cultured Human Endothelial Cells", John M. Hartan et al., The Journal of Cell Biology. vol. 103, Sep. 1986, pp. 1129–1133.
"Endothelial Leukocyte Adhesion Molecule 1: An Inducible Receptor for Neutrophils Related to Complement Regulatory Proteins and Lectins", Michael P. Bevilacque et al., Science, vol. 243, Mar. 1989, pp. 1160–1164.
"Enhancement of Incisional Wound Healing and Neovascularization in Normal Rats by Thrombin and Synthetic Thrombin Receptor–Activating Peptides", D.H. Carney et al., The American Society for Clinical Investigation, Inc., vol. 89, May. 1992, pp. 1469–1477.

*Primary Examiner*—Christopher S. F. Low
*Assistant Examiner*—David Lukton

(57) ABSTRACT

The invention is directed to substituted heterocyclic acyl-tripeptides useful as thrombin receptor modulators, their use in wound healing and preventing platelet aggregation. Pharmaceutical compositions comprising the substituted heterocyclic acyl-tripeptides of the present invention and methods of treating conditions mediated by the thrombin receptor are also disclosed.

9 Claims, No Drawings

SUBSTITUTED HETEROCYCLIC ACYL-TRIPEPTIDES USEFUL AS THROMBIN RECEPTOR MODULATORS

FIELD OF THE INVENTION

The present application is a continuation-in-part of Ser. No. 09/444,327 that was filed on Nov. 19, 1999 (hereby incorporated by reference herein) now abandonded which claims priority from provisional patent application Serial No. 60/112,313, filed on Dec. 14, 1998.

BACKGROUND OF THE INVENTION

Thrombin is an important serine protease in hemostasis and thrombosis. One of the key actions of thrombin is receptor activation. A functional human thrombin receptor (TR), cloned by Coughlin in 1991 (T.-K. Vu, *Cell* 1991, 64, 1057), was found to be a member of the G-protein coupled receptor (GPCR) superfamily. The receptor activation putatively occurs by N-terminal recognition and proteolytic cleavage at the Arg-41/Ser-42 peptide bond to reveal a truncated N-terminus. This new receptor sequence, which has an SFLLRN (Ser-Phe-Leu-Leu-Arg-Asn SEQ. ID. No. 1) N-terminus acting as a tethered ligand to recognize a site on the receptor, can trigger activation and signal transduction leading to platelet aggregation. Peptide analogues based on this hexapeptide have also shown good agonist activity leading to platelet aggregation. Since 1991, two other protease-activated receptors with extensive homology to the thrombin receptor, "PAR-2" and "PAR-3," were cloned, and found to be activated by similar N-terminal hexapeptide sequences. Hence, agonists/antagonists of the thrombin receptor, such as those included in this invention, may be useful in activating/antagonizing these protease-activated receptors as well.

Activation of the thrombin receptor by agonist compounds of this invention may mimic thrombins role in tissue repair. Thrombin can initiate effects related to wound healing, such as: increasing vascular permeability to allow entry of cells and fluid into injured tissue (A. B. Malik, *Semin. Thromb. Haemostasis* 1986, 184); increasing the synthesis of PDGF by endothelial cells (J. M. Harlan, *J. Cell Biol.* 1986, 103, 1129); and increasing the adhesion of platelets, monocytes, and neutrophils to endothelial cells (M. P. Bevilacqua, *Science* 1989, 243, 1160). Tissue repair in rats following surgical incision is accelerated by the use of thrombin (D. H. Carney, *J. Clin. Invest.* 1992, 89, 1469). Thus, agonists at the thrombin receptor may be useful as wound healing agents or in tissue repair.

The peptide-based antagonists of the thrombin receptor in this present invention may show efficacy against myocardial infarction, stroke, restenosis, angina, atherosclerosis, and ischemic attacks by virtue of their ability to prevent platelet aggregation. The thrombin receptor has also been identified on other cell types: endothelial, fibroblast, osteosarcoma, smooth muscle, and neuronal/glia. Thrombin activation of endothelial cells upregulates P-selectin to induce polymorphonuclear leukocyte adhesion—an inflammatory response of the vessel wall (Y. Sugama, *J. Cell Biol.* 1992, 119, 935). In fibroblasts, thrombin receptor activation induces proliferation and transmission of mitogenic signals (D. T. Hung, *J. Cell Biol.* 1992, 116, 827). Thrombin has been implicated in osteoblast proliferation through its activation of osteoblast cells (D. N. Tatakis, *Biochem. Biophys. Res. Commun.* 1991, 174, 181). Thrombin has been implicated in the regulation and retraction of neurons (K. Jalink, *J. Cell. Biol.* 1992, 118, 411). Therefore, in this context, the antagonist compounds of this invention may also be useful against inflammation, restenosis, cancer, osteoporosis, and neurodegenerative disorders.

SUMMARY OF THE INVENTION

The present invention is directed to compounds represented by the following general formula (I):

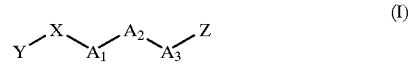

wherein $A_1$, $A_2$, $A_3$, X, Y, and Z are defined later.

These compounds are thrombin receptor modulators and may be useful either as agonists in wound healing and tissue repair or as antagonists in myocardial infarction, stroke, restenosis, angina, atherosclerosis, ischemic attacks, inflammation, cancer, osteoporosis, or neurodegenerative disorders.

DETAILED DESCRIPTION OF THE INVENTION

More particularly, the present invention is directed to compounds of the following formula (I):

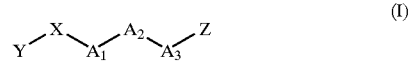

wherein $A_1$ is an alkyl amino acid residue selected from Cha, Leu and Ile, an amino alkyl amino acid residue selected from Arg and Lys, or an aryl amino acid residue selected from Phe, substituted Phe, Tyr, or Trp;

$A_2$ is an amino alkyl amino acid residue selected from Lys, Orn, Arg, and homo Arg;

$A_3$ is an aryl amino acid residue selected from Phe, substituted Phe, Tyr, Trp, phenyl-Gly, 2-thienyl-Ala and 3-thienyl-Ala, an alkyl amino acid residue selected from Cha, Leu and Ile, an amido alkyl amino acid selected from Asn and Gln, or an amino alkyl amino acid residue selected from Arg, homo Arg, Orn and Lys;

X is selected from CO, CS, or $SO_2$;

Y is selected from aryl, substituted aryl, heterocycloalkyl, substituted heterocycloalkyl, heteroaryl, substituted heteroaryl, heteroarylethylenyl, substituted heteroarylethylenyl, arylacrylamidoheteroaryl, substituted arylacrylamidoheteroaryl, heteroarylacrylamidoheteroaryl and substituted heteroarylacrylamidoheteroaryl, preferably, Y is not pyrrolidinyl, substituted pyrrolidinyl, phenyl or 2-aminophenyl; most preferably, Y is selected from heteroaryl, substituted heteroaryl, arylacrylamidoheteroaryl, and substituted arylacrylamidoheteroaryl;

Z is selected from $NH_2$, NH-alkyl, NH-aralkyl, or an amino alkyl amino acid residue selected from Arg-$NH_2$; and wherein all amino acids are of the L configuration;

and the pharmaceutically acceptable salts thereof.

In the compounds of formula (I), the amino acid residues comprising the $A_1$, $A_2$, and $A_3$ substituents are attached to the adjacent moiety according to standard nomenclature so that the amino-terminus (N-terminus) of the amino acid is drawn on the left and the carboxy-terminus of the amino acid is drawn on the right. So, for example, in Compound 1, where $A_1$ is Cha, $A_2$ is Arg and $A_3$ is Phe, the N-terminus of the Cha ($A_1$) is attached to the X substituent and the carboxy-terminus of the Cha ($A_1$) is attached to the N-terminus of the $A_2$ substituent (Arg), similarly, the the N-terminus of the Arg ($A_2$) is attached to the carboxy-terminus of the $A_1$ substituent and the carboxy-terminus of the Arg ($A_2$) is attached to the N-terminus of the $A_3$ substituent (Phe), similarly, the N-terminus of the Phe ($A_3$) is attached to the carboxy-terminus of the $A_2$ substituent and the carboxy-terminus of the Phe ($A_3$) is attached to the Z substituent.

When a particular group is "substituted" (e.g., Phe, heterocycloalkyl, heteroaryl, acrylamidoheteroaryl), that group may have from 1 to 4 substituents independently selected from: halo (I, Br, Cl, F), $C_1$–$C_8$ alkyl, $C_1$–$C_8$ alkoxy, amino, amido, carboxyl, cyano, nitro, fluorinated $C_1$–$C_8$ alkyl, fluorinated $C_1$–$C_8$ alkoxy, or aryl (preferably, phenyl or substituted phenyl).

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, unless otherwise noted alkyl and alkoxy whether used alone or as part of a substituent group, include straight and branched chains having 1 to 8 carbon atoms, or any number within this range. For example, alkyl radicals include methyl, ethyl, propyl, isopropyl, n-butyl, isobutyl, sec-butyl, t-butyl, n-pentyl, 3-(2-methyl)butyl, 2-pentyl, 2-methylbutyl, neopentyl, n-hexyl, 2-hexyl and 2-methylpentyl. Alkoxy radicals are oxygen ethers formed from the previously described straight or branched chain alkyl groups. Cycloalkyl groups contain 3 to 8 ring carbons and preferably 5 to 7 carbons. Similarly, alkenyl and alkynyl groups include straight and branched chain alkenes and alkynes having 1 to 8 carbon atoms, or any number within this range.

The term "aryl" as used herein, alone or in combination with other terms, represents an aromatic hydrocarbon group. Examples of aryl groups include, but are not limited to, phenyl, naphthyl, phenanthryl, anthryl, biphenylenyl, fluorenyl, or azulenyl. Preferred aryl groups include phenyl, naphthyl and biphenylenyl.

The term "heterocycloalkyl" as used herein represents an unsubstituted or substituted stable three to seven membered monocyclic saturated ring system which consists of carbon atoms and from one to three heteroatoms selected from N, O or S, and wherein the nitrogen or sulfur heteroatoms may optionally be oxidized, and the nitrogen heteroatom may optionally be quaternized. The heterocyloalkyl group may be attached at any heteroatom or carbon atom which results in the creation of a stable structure. Examples of such heterocyloalkyl groups include, but are not limited to azetidinyl, piperidinyl, piperazinyl, oxopiperazinyl, oxopiperidinyl, oxoazepinyl, azepinyl, tetrahydrofuranyl, dioxolanyl, tetrahydroimidazolyl, tetrahydrooxazolyl, tetrahydropyranyl, morpholinyl, thiomorpholinyl, thiamorpholinyl sulfoxide, thiamorpholinyl sulfone and oxadiazolyl.

The term "heteroaryl" as used herein represents an unsubstituted or substituted stable five or six membered monocyclic aromatic ring system or an unsubstituted or substituted nine or ten, membered benzo-fused heteroaromatic ring system which consists of carbon atoms and from one to three heteroatoms selected from N, O or S, and wherein the nitrogen or sulfur heteroatoms may optionally be oxidized, and the nitrogen heteroatom may optionally be quaternized. The heteroaryl group may be attached at any heteroatom or carbon atom which results in the creation of a stable structure. Examples of heteroaryl groups include, but are not limited to pyridyl, pyridazinyl, thienyl, furanyl, imidazolyl, isoxazolyl, oxazolyl, pyrazolyl, pyrrolyl, thiazolyl, thiadiazolyl, triazolyl, benzimidazolyl, benzofuranyl, benzothienyl, benzisoxazolyl, benzoxazolyl, benzopyrazolyl, indolyl, benzothiazolyl, benzothiadiazolyl, benzotriazolyl or quinolinyl. Prefered heteroaryl groups include pyridyl, pyrrolyl, pyrazinyl, thiadiazolyl, pyrazolyl, thienyl, triazolyl and quinolinyl.

The term "aralkyl" means an alkyl group substituted with an aryl group (e.g., benzyl, phenylethyl). Similarly, the term "aralkoxy" indicates an alkoxy group substituted with an aryl group (e.g., benzyloxy).

The term "acyl" as used herein means an organic radical having 1 to 6 carbon atoms (branched or straight chain) derived from an organic acid by removal of the hydroxyl group.

The term "amido" refers to the group C(O)NH or C(O)$NH_2$.

The term "carbonyl" refers to the group C(O).

The term "arylacrylamidoheteroaryl" as used herein means an aryl group attached to an ethylene which is attached to an amido group which is attached to a heteroaryl group, where the terms "aryl", "amido" and "heteroaryl" are as defined above. The term "arylacrylamidoheteroaryl" can therefore refer to a group such as Aryl-C=C—C(O)—NH-heteroaryl, with a specific example of such an "arylacrylamidoheteroaryl" group being 5-($\chi$-Me-cinnamamido) triazol-3-yl O having the structure

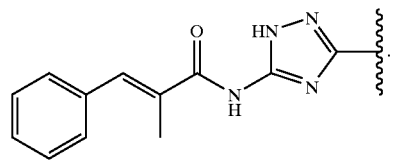

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques know in the art as well as those methods set forth herein.

As used herein, the term "composition" is intended to encompass a product comprising the specified ingredients in the specified amounts, as well as any product which results, directly or indirectly, from combinations of the specified ingredients in the specified amounts.

The compounds of the present invention may also be present in the form of a pharmaceutically acceptable salt. The pharmaceutically acceptable salt generally takes a form in which the nitrogen of the amino-substituted heterocycle or an amino-acid's basic side-chain is protonated with an inorganic or organic acid. Representative organic or inorganic acids include hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benezenesulfonic, oxalic, pamoic, 2-naphthalenesulfonic, p-toluenesulfonic, cyclohexanesulfamic, salicylic, saccharinic or trifluoroacetic.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention.

Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

Until the present invention by Applicants, the known thrombin receptor agonists were peptides (i.e., PAR-1 peptide agonists) having a minimum sequence length of five amino acids. Applicants have unexpectantly discovered the instant thrombin receptor agonists which are significantly truncated or that contain a heterocycle within the peptide backbone as a peptidomimetic unit.

Particularly preferred compounds of the present invention that could be useful as thrombin receptor agonists include those compounds shown in Table 1, which shows $EC_{50}$ values for platelet aggregation and binding $IC_{50}$ at the thrombin receptor. Amino acids bear the "L" absolute configuration unless denoted otherwise.

TABLE 1

$$Y-\overset{O}{\underset{\|}{C}}-A_1-A_2-A_3-NH_2$$

| # | Y | $A_1$ | $A_2$ | $A_3$ | $EC_{50}(M)$ | Bndg(M) |
|---|---|---|---|---|---|---|
| 1 | 5-$H_2$N-1,2,4-triazol-3-yl | Cha | Arg | Phe | 0.75 | 1.9 |
| 2 | 5-Bromopyridin-3-yl | Cha | Arg | Phe | 0.46 | 1.7 |
| 3 | 2-Chromonyl | Cha | Arg | Phe | 0.51 | 1.6 |
| 4 | 5-(α-Me-cinnamamido)triazol-3-yl | Cha | Arg | Phe | 0.76 | 4.2 |
| 5 | 5-Naphthylacrylamidotriazol-3-yl | Cha | Arg | Phe | 0.99 | 16 |
| 6 | Quinoxalin-2-yl | Cha | Arg | Phe | 1.03 | 3.1 |
| 7 | 5-(o-Cl-cinnamamido)triazol-3-yl- | Cha | Arg | Phe | 1.14 | 1.4 |
| 8 | 6-Aminopyridin-3-yl | Cha | Arg | Phe | 1.24 | 2.0 |
| 9 | 5-$H_2$N-1,2,4-triazol-3-yl | Cha | Arg | Phe-Arg | 1.21 | 0.5 |
| 10 | Thiadiazol-4-yl | Cha | Arg | Phe | 1.28 | 9.4 |
| 11 | 5-(2,3-diMeO-cinnamamido)triazol-3-yl | Cha | Arg | Phe | 1.64 | 6.4 |
| 12 | 5-(α-F-cinnamamido)triazol-3-yl | Cha | Arg | Phe | 1.72 | 2.2 |
| 13 | 5-(m-$NO_2$-cinnamamido)triazol-3-yl | Cha | Arg | Phe | 1.89 | 8.5 |
| 14 | 5-(o-$NO_2$-cinnamamido)triazol-3-yl | Cha | Arg | Phe | 1.89 | 1.6 |
| 15 | Pyridin-3-yl | Cha | Arg | Phe | 1.97 | 1.3 |
| 16 | 5-(m-Cl-cinnamamido)triazol-3-yl | Cha | Arg | Phe | 2.38 | 15 |
| 17 | 5-$H_2$N-1,2,4-triazol-3-yl | Phe | Arg | Phe | 2.4 | 2.1 |
| 18 | 5-$H_2$N-1,2,4-triazol-3-yl | Cha | Lys | Phe | 2.67 | 5.4 |
| 19 | 5-$H_2$N-1,2,4-triazol-3-yl | Cha | Arg | Cha | 2.8 | 2.0 |
| 20 | 5-$H_2$N-1,2,4-triazol-3-yl | Cha | Arg | Phgly | 3.13 | 7.1 |
| 21 | 5-(thiophen-2-ylacrylamido)triazol-3-yl | Cha | Arg | Phe | 2.9 | 4.4 |
| 22 | 3-$H_2$N-pyrazin-2-yl | Cha | Arg | Phe | 4.2 | 8.5 |
| 23 | trans 2-(3-pyridyl)ethylenyl | Cha | Arg | Phe | 2.6 | 5.5 |
| 24 | 5-(p-MeO-cinnamamido)triazol-3-yl | Cha | Arg | Phe | 5.6 | 4 |
| 25 | 5-(p-CN-cinnamamido)triazol-3-yl | Cha | Arg | Phe | 5.8 | 31 |
| 26 | 5-(p-F-cinnamamido)triazol-3-yl | Cha | Arg | Phe | 7.9 | 1.7 |
| 27 | 2-$H_2$N-pyridin-3-yl | Cha | Arg | Phe | 8.8 | 2.3 |
| 28 | 5-$H_2$N-1,2,4-triazol-3-yl | Cha | Arg | Tyr | 9.7 | 6 |
| 29 | 5-$H_2$N-1,2,4-triazol-3-yl | Cha | Arg | 2-Thala | 11 | 4 |
| 30 | Pyridin-2-yl | Cha | Arg | Phe | 14 | 4 |
| 31 | 5-(p-Phenyl-cinnamamido)triazol-3-yl | Cha | Arg | Phe | 25 | 12 |
| 32 | N-(p-F-phenylalanyl)-piperidin-3-yl | Cha | Arg | Phe | 26 | 2 |
| 33 | 5-(Cinnamamido)triazol-3-yl | Cha | Arg | Phe | 28 | 6 |
| 34 | 5-(α-phenyl-cinnamamido)triazol-3-yl | Cha | Arg | Phe | 28 | 3 |
| 38 | 3-aminophenyl | Cha | Arg | Phe | 2.9 | 2 |
| 39 | 1-biphenyl | Cha | Arg | Phe | (56%)[1] | 13 |
| 40 | 2-biphenylenyl | Cha | Arg | Phe | 1.2 | 2.4 |
| 41 | benzimidazol-5-yl | Cha | Arg | Phe | 4 | 4 |

[1]Percent aggregation induced at 50 M.

Particularly preferred compounds of the present invention that could be useful as thrombin receptor antagonists or mixed agonists/antagonists include those compounds shown in Table 2, which shows IC$_{50}$ values for inhibition of platelet aggregation (gel-filtered platelets aggregation induced by thrombin) and binding IC$_{50}$ at the thrombin receptor. Amino acids bear the "L" absolute configuration unless denoted otherwise.

TABLE 2

$$Y\diagdown^{X}\diagup^{A_2}\diagdown_{Phe}\diagup^{NH_2}$$

| # | X | A1 | A2 | X | IC$_{50}$(M) | Bndg(M) |
|---|---|---|---|---|---|---|
| 7 | 5-(o-Cl-cinnamamido)triazol-3-yl | Cha | Arg | CO | 3.6 | 1.4 |
| 21 | 5-(Thien-2-ylacrylamido)triazol-3-yl | Cha | Arg | CO | 5.4 | 4.4 |
| 33 | 5-(Cinnamamido)triazol-3-yl | Cha | Arg | CO | 9.8 | 6.4 |
| 4 | 5-(α-Me-cinnamamido)triazol-3-yl | Cha | Arg | CO | 14 | 4.2 |
| 34 | 5-(α-Ph-cinnamamido)triazol-3-yl | Cha | Arg | CO | 19 | 3.1 |
| 35 | 6-Cinnamamidopyridin-3-yl | Cha | Arg | CO | 26 | 2.2 |
| 36 | 5-Cl, X3-Me-benzothiophen-2-yl | Cha | Arg | SO$_2$ | 8.4 | 4.6 |
| 26 | 5-(p-F-cinnamamido)triazol-3-yl | Cha | Arg | CO | 1 3 | 1.7 |
| 37 | Benzothiophen-2-yl | Cha | Arg | CO | 21 | 2.3 |
| 42 | 1-naphthyl | Cha | Arg | SO$_2$ | 7.8 | 1.7 |
| 43 | 2-naphthyl | Cha | Arg | SO$_2$ | 12.5 | 2.1 |

Particularly preferred compounds of the present invention are:

(5-Bromopyridin-3-yl)carbonyl-cyclohexylalanyl-arginyl-phenylalanineamide;
2-Chromonylcarbonyl-cyclohexylalanyl-arginyl-phenylalanineamide;
(5-Aminotriazol-3-yl)carbonyl-cyclohexylalanyl-arginyl-phenylalanineamide;
[5-(χ-Methyl)cinnamamidotriazol-3-yl]carbonyl-cyclohexylalanyl-arginyl-phenylalanineamide;
{5-[3-(1-Naphthyl)acrylamido]triazol-3-yl}carbonyl-cyclohexylalanyl-arginyl-phenylalanineamide;
[Quinoxalin-2-yl]carbonyl-cyclohexylalanyl-arginyl-phenylalanineamide;
[5-(o-Chlorocinnamamido)triazol-3-yl]carbonyl-cyclohexylalanyl-arginyl-phenylalanineamide;
(6-Aminopyridin-3-yl)carbonyl-cyclohexylalanyl-arginyl-phenylalanineamide;
(5-Aminotriazol-3-yl)carbonyl-phenylaianyl-arginyl-phenylalanyl-arginineamide;
(5-Aminotriazol-3-yl)carbonyl-cyclohexylalanyl-lysinyl-phenylalanineamide;
{5-[3-(2-Thienyl)acrylamido]triazol-3-yl}carbonyl-cyclohexylalanyl-arginyl-phenylalanineamide;
[5-cinnamamidotriazol-3-yl]carbonyl-cyclohexylalanyl-arginyl-phenylalanineamide;
(6-Cinnamamidopyridin-3-yl)carbonyl-cyclohexylalanyl-arginyl-phenylalanineamide; or
(5-Chloro-3-methyl-benzothiophen-2-yl)carbonyl-cyclohexylalanyl-arginyl-phenylalanineamide;

and pharmaceutically acceptable salts thereof.

The modulators of this invention may be prepared using solid phase chemistry as shown in Scheme A.

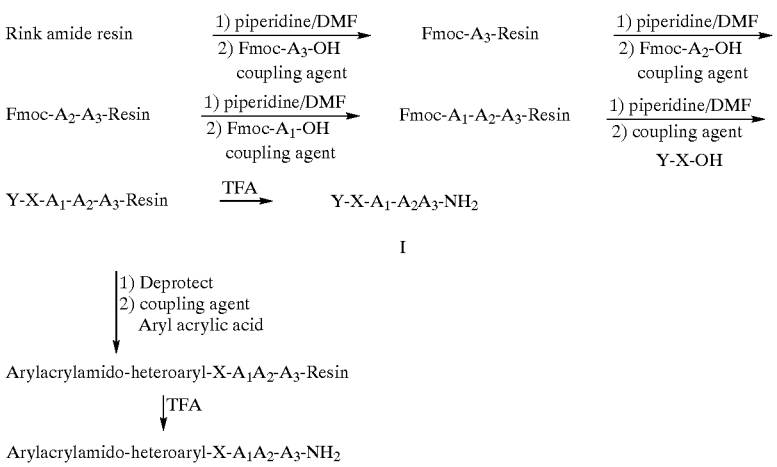

Thus, the resin is Fmoc deprotected via agitation using piperidine or any dialkyl amine in an appropriate solvent such as DMF, washed with fresh solvent and then coupled with an Fmoc protected amino-acid $A_3$ using suitable coupling reagents such as diisopropylcarbodiimide (DIC) or dicyclohexylcarbodiimide (DCC) or Bis(2-oxo-3-oxazolidinyl)phosphinic chloride (BOP-Cl) along with hydroxybenzotriazole (HOBT) in DMF or another dipolar aprotic solvent. After washing, the amino-acid loaded resin is Fmoc deprotected as above with a dialkyl amine in DMF and coupled again with the second Fmoc protected amino-acid $A_2$ with a coupling agent as above. This Fmoc dipeptido loaded resin is further deprotected with dialkylamine in DMF, or appropriate solvent, and coupled again to the Fmoc amino-acid $A_1$ using a coupling agent as above. The triptido resin is deprotected with a dialkyl amine in DMF and coupled to the substituted acid Y—X—OH with an appropriate coupling agent. At this point the product may be cleaved from the resin using a strong acid such as trifluoroacetic (TFA) acid in any inert solvent, such as DCM, to give the peptide amide I. However, if the Y group possesses a protected amino functionality, such as Fmoc-amino, this may be deprotected and the amino-peptide product cleaved from the resin or the freed-up amine can be reacted further prior to cleavage of the peptide from the resin. Thus, the Fmoc can be removed using a dialkyl amine in DMF as above and the amino-peptide can be 1) cleaved from the resin with TFA or 2) coupled with an aryl acrylic acid, using appropriate coupling agent such as BOP-Cl, and the product can be cleaved from the resin with TFA to afford peptide II. Following this general route, preparation of compound 1 as outlined in Scheme 1 is prepared, as described in more detail in the experimental section.

Scheme 1:

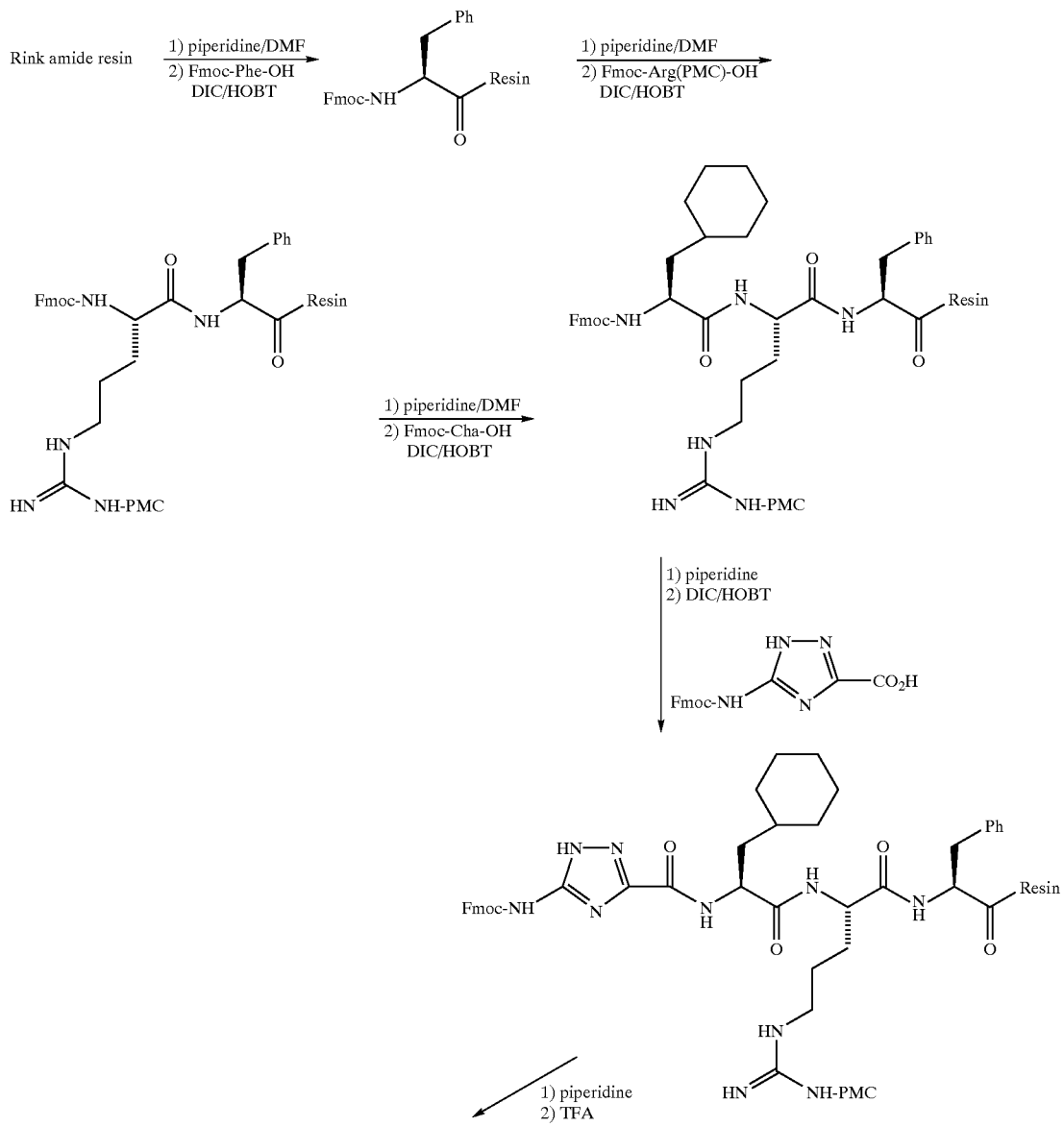

-continued

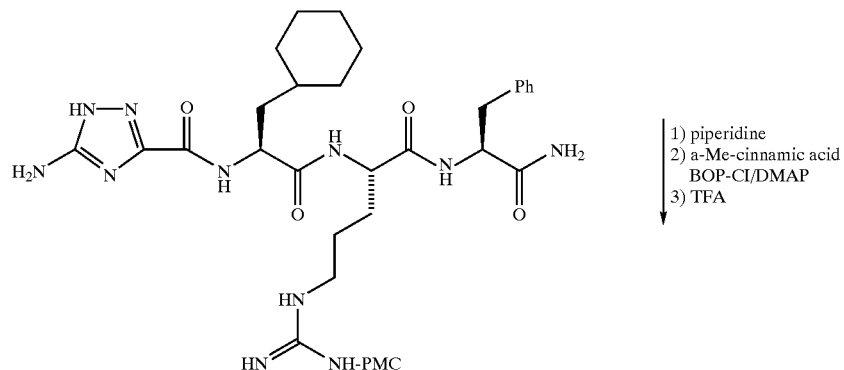

1

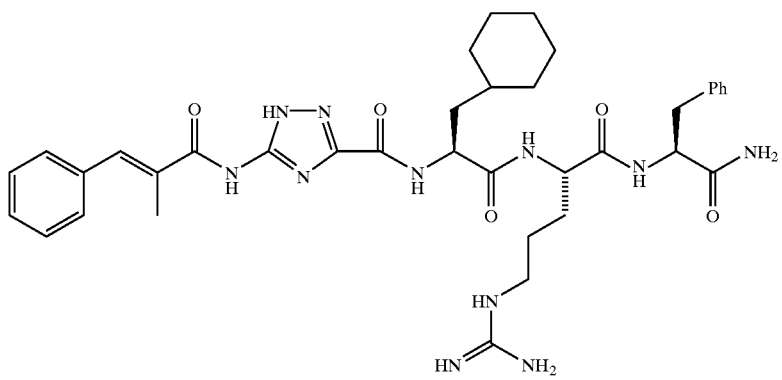

4

Alternatively, the compounds may be prepared via normal solution phase chemistry as shown in Scheme B.

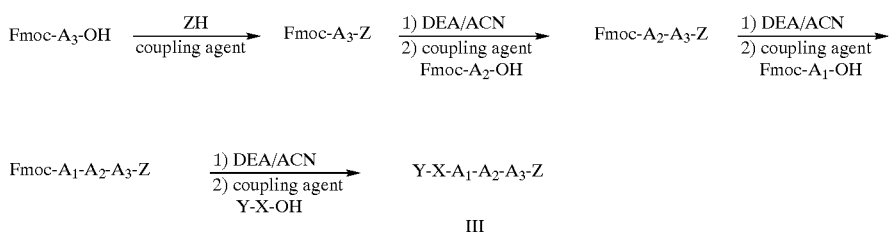

Thus, Fmoc protected amino-acid $A_3$ can be coupled with an amine ZH using the normal peptide coupling agents such as DIC or DCC and HOBT in dipolar aprotic solvents such as acetonitrile (ACN) or dimethyl formamide (DMF). The isolated product can then be Fmoc deprotected with diethylamine (DEA), or another dialkyl amine, in a dipolar aprotic solvent such as ACN, and the resultant amine coupled to the second Fmoc protected amino-acid $A_2$. This dipeptide can similarly be deprotected as above and coupled with an appropriate coupling agent with Fmoc protected amino-acid $A_1$ to give the Fmoc-tripeptide. Deprotection of the Fmoc group with a dialkyl amine is followed by coupling of this tripeptide to the acid Y—X—OH using a coupling agent such as DIC with HOBT to give the product III. Using this general route, synthesis of compound 2 was prepared as outlined in Scheme 2, and further described in the experimental section.

Scheme 2:

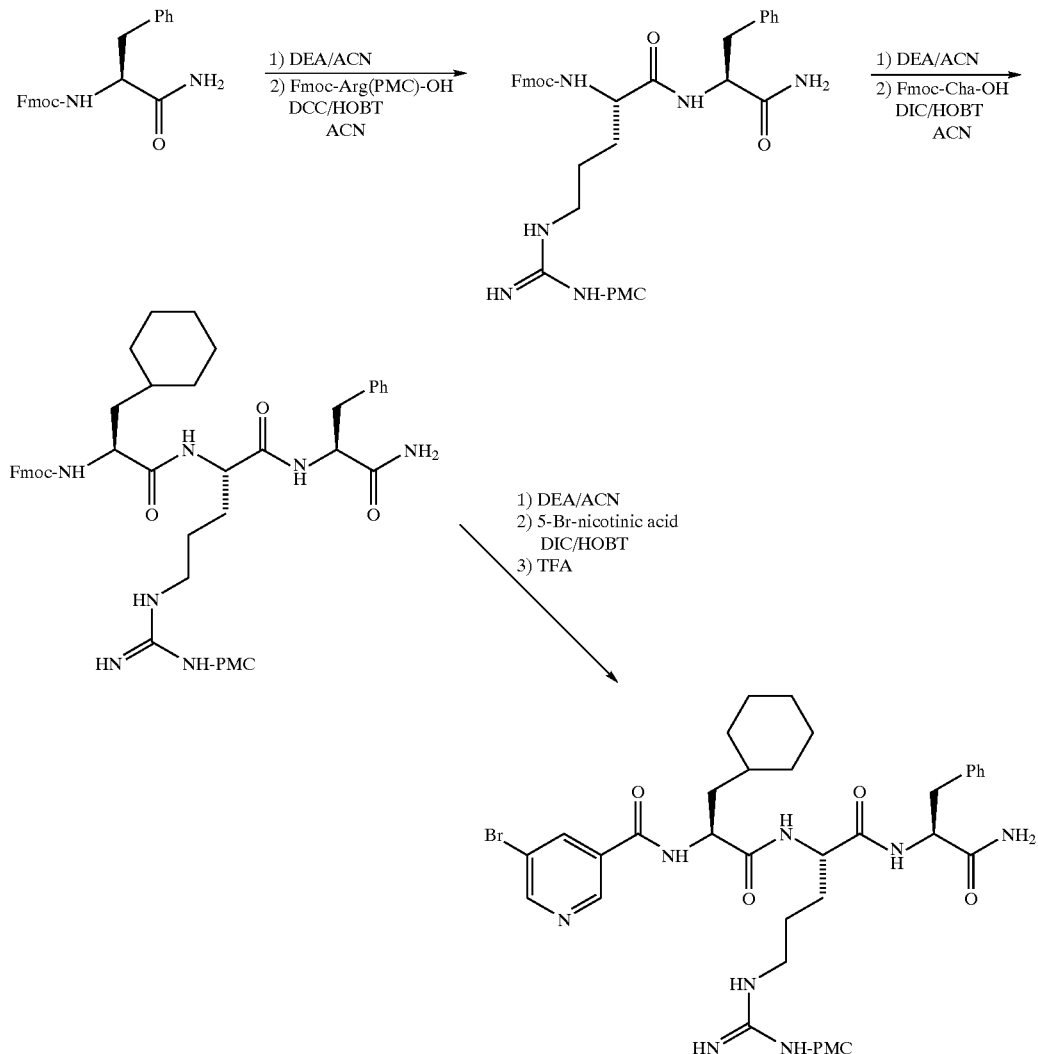

The utility of the compounds of formula (I) to act as thrombin receptor modulators can be determined according to the procedures described in Examples 4 to 5 herein. The present invention therefore provides a method of treating a condition mediated by modulation of the thrombin receptor in a subject in need thereof which comprises administering any of the compounds or pharmaceutical compositions as defined herein in a quantity effective to treat the condition. Additionally, the present invention includes the use of a compound of formula (I) for the preparation of a medicament for the treatment of a condition mediated by modulation of the thrombin receptor. The compound may be administered to a patient by any conventional route of administration, including, but not limited to, intravenous, oral, subcutaneous, intramuscular, intradermal and parenteral.

The present invention also provides pharmaceutical compositions comprising one or more compounds of this invention in association with a pharmaceutically acceptable carrier.

To prepare the pharmaceutical compositions of this invention, one or more compounds of formula (I) or salt thereof of the invention as the active ingredient, is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.03 mg to 100 mg/kg (preferred 0.1–30 mg/kg) and may be given at a dosage of from about 0.1–300 mg/kg/day (preferred 1–50 mg/kg/day). The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be seperated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their components enantiomers by standard techniques, such as the formation of diastereomeric pairs by salt formation with an optically active acid, such as (−)-di-p-toluoyl-d-tartaric acid and/or (+)-di-p-toluoyl-I-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis,* John Wliey & Sons, 1991. The protecting groups may be removed at a convenient subsequent stage using methods known from the art.

The method of treating conditions modulated by the thrombin receptor described in the present invention may also be carried out using a pharmaceutical composition comprising any of the compounds as defined herein and a pharmaceutically acceptable carrier. The pharmaceutical composition may contain between about 0.01 mg and 100 mg, preferably about 5 to 50 mg, of the compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixers, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methylcellulose and the like. For parenteral administration, sterile suspensions and solutions are desired. Isotonic preparations which generaly contain suitable preservatives are employed when intravenous administration is desired.

The compound of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine or phophatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxy-ethylaspartamidephenol, or polyethyl eneoxidepolylysine substituted with palmitoyl residue. Furthermore, the compounds of the present invention may be coupled to a class of biodegradable polymers useful in achieving controlled release of a drug, for example, polylactic acid, polyepsilon caprolactone, polyhydroxy butyeric acid, polyorthoesters, polyacetals, polydihydropyrans, polycyanoacrylates and cross-linked or amphipathic block copolymers of hydrogels.

Compounds of this invention may be administered in any of the foregoing compositions and according to dosage regimens established in the art whenever treatment of thrombotic disorders is required.

The daily dosage of the products may be varied over a wide range from 0.01 to 1,000 mg per adult human per day. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. An effective amount of the drug is ordinarily supplied at a dosage level of from about 0.1 mg/kg to about 300 mg/kg of body weight per day. Preferably, the range is from about 1 to about 50 mg/kg of body weight per day. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

To prepare the pharmaceutical compositions of this invention, one or more compounds of formula (I) or salt thereof of the invention as the active ingredient, is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.03 mg to 100 mg/kg (preferred 0.1–30 mg/kg) and may be given at a dosage of from about 0.1–300 mg/kg/day (preferred 1–50 mg/kg/day). The dosages, however, may be varied depending upon the requirement of the patients, the severity of the condition being treated and the compound being employed. The use of either daily administration or post-periodic dosing may be employed.

The following Examples are set forth to aid in the understanding of the invention, and are not intended and should not be construed to limit in any way the invention set forth in the claims which follow thereafter.

Protected amino acids were purchased from Novabiochem, Synthetech or Bachem Bioscience Inc. All other chemicals were purchased from Aldrich Chemical Company, Inc. High field $^1$H NMR spectra were recorded on a Bruker AC-300 spectrometer at 300 MHz, and coupling constants are given in Herz. Microanalyses were performed at Robertson Microlit Laboratories, Inc., Madison, N.J. In the examples and throughout this application, the following abbreviations have the meanings recited hereinafter:

| | |
|---|---|
| ACN | Acetonitrile |
| BOP-Cl | Bis(2-oxo-3-oxazolidinyl)phosphinic chloride |
| DCM | Dichloromethane |
| DCC | Dicyclohexylcarbodiimide |
| DIC | Diisopropylcarbodiimide |
| DEA | Diethylamine |
| DMAP | 4-Dimethylaminopyridine |
| DMF | N,N-Dimethylformamide |
| Et$_2$O | Diethyl ether |
| Fmoc | Fluorenylmethoxycarbonyl |
| HOBT | Hydroxybenzotriazole |
| Me | Methyl |
| Ph | Phenyl |
| Pmc | 2,2,5,7,8-Pentamethylchroman-6-sulfonyl |
| RT | room temperature |
| TFA | Trifluoroacetic acid |

Amino acid abbreviations are defined below:

| | |
|---|---|
| Arg | Arginine |
| Asn | Asparagine |
| Cha | Cyclohexylalanine |
| Gln | Glutamine |
| hArg | Homoarginine |
| hPhe | Homophenylalanine |
| Ile | Isoleucine |
| Leu | Leucine |
| Lys | Lysine |
| Orn | Ornithine |
| Phe | Phenylalanine |
| Phgly | Phenylglycine |
| 2-Thala | 2-Thienylalanine |
| 3-Thala | 3-Thienylalanine |
| Trp | Tryptophan |
| Tyr | Tyrosine |

EXAMPLE 1

N-(5-Amino-1,2,4-triazol-3-yl)carbonyl)-cyclohexylalanyl-argininyl-phenylalanine amide (1)

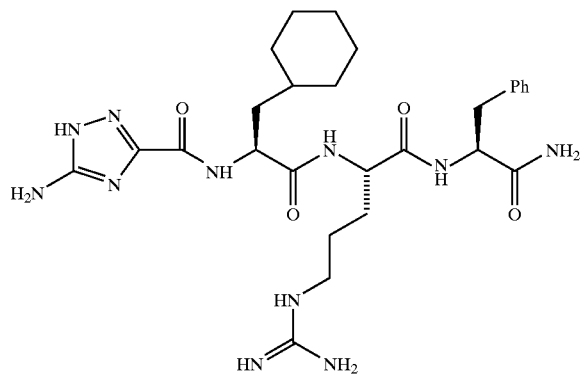

1

Rink amide resin (4.0 g, 3.24 mm) was placed in a solid phase hour-glass reactor and agitated (nitrogen bubbling) with 20% piperidine/DMF (25 mL) for 1 hr. The solution was drained off and the resin was washed with DMF (4×), DCM (3×), and DMF (3×). The resin was combined with Fmoc-Phe-OH (3.77 g, 9.75 mm), HOBT (1.5 g, 9.75 mm) and DIC (1.23 g, 9.75 mm) in DMF (25 mL) and agitated in the reactor for 16 hr at ambient temperature. The solution was drained and resin was washed with DMF (5×) and DCM (4×) and dried in vacuo. A portion (1.0 g, 0.80 mm) was agitated in the reactor at ambient temperature with 20% piperidne/DMF (15 mL) for 1 hr, the solution was drained and resin washed with DMF (4×), DCM (3×), and DMF (3×). This was combined with Fmoc-Arg(Pmc)-OH (1.84 g, 2.4 mm), HOBT (0.37 g, 2.4 mm), and DIC (0.31 g, 2.4 mm) in DMF (10 mL) and agitated at ambient temperature for 16 hr. After draining the solution, the resin was washed with DMF (4×), and DCM (3×). Half of this batch was washed with DMF (3×) and then agitated with 20% piperidine/DMF (10 mL) for 1 hr. The solution was drained and the resin was washed with DMF (4×), DCM (3×), and DMF (3×) and then combined with Fmoc-Cha-OH (0.47 g, 1.2 mm), HOBT (0.18 g, 1.2 mm) and DIC (0.15 g, 1.2 mm) in DMF (10 mL) and agitated for 16 hr at ambient temperature. The solution was drained and the resin was washed with DMF (4×), DCM (3×), and DMF (3×) and treated with 20% piperidine/DMF for 1 hr. The solution was drained and the resin was washed with DMF (4×) and then combined with Fmoc-3-amino-1,2,4 triazole-5-carboxylic acid (0.42 g, 1.2 mm), HOBT (0.18 g, 1.2 mm), and DIC (0.15 g, 1.2 mm) in DMF (10 mL) and agitated at ambient temperature for 16 hr. The solution was drained off, and the resin was washed with DMF (4×), DCM (3×), and DMF (3×) and then agitated with 20% piperidine/ DMF (15 mL) for 1 hr. The solution was drained and the resin was washed with DMF (4×), and DCM (3×) and dried under a nitrogen stream. The resin was then agitated with 99% TFA (20 mL) at ambient temperature for 1.5 hr. The TFA solution was collected and evaporated in vacuo to an oil, which was triturated with $Et_2O$ (3×) to give a white solid (152 mg). Purification was accomplished via reverse phase HPLC using 0.16% TFA in ACN/0.20% TFA in water (35:65) and upon lyophilization afforded white floccular solid 1 (120 mg). Anal. calcd. for $C_{27}H_{41}N_{11}O_4 \cdot 2.25$ TFA·1.0 $H_2O$ (858.26): C, 44.08; H, 5.13; N, 17.95; F, 14.94. Found: C, 43.82; H, 5.27; N, 17.91; F, 14.50. FAB-MS m/e 584.9 ($MH^+$). $^1H$ NMR ($DMSO/D_2O$) 7.25 (m, 5H), 4.5 (dd, 1H), 4.4 (dd, 1H), 4.28 (dd, 1H), 3.1–2.95 (m, 3H), 2.8 (dd, 1H), 1.8–1.35 (m, 11H), 1.3–1.0 (m, 4H), 0.9 (m, 2H).

EXAMPLE 2

N-(5-Bromopyridin-3-yl-carbonyl)-cyclohexylalanyl-argininyl-phenylalanine amide (2)

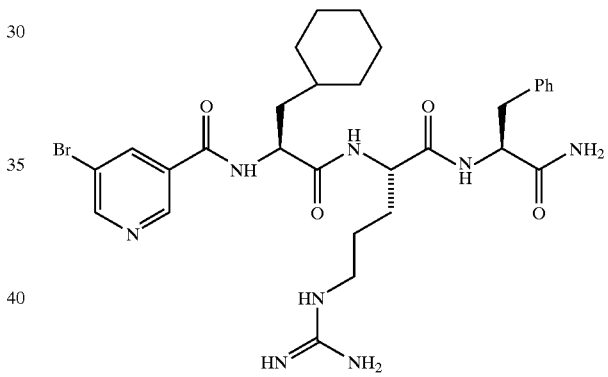

2

Fmoc-phenylalanine amide (3.87 g, 10 mm) was stirred in ACN (100 mL) and DEA (5 mL) was added and stirred at RT for 1 hr. The solution was evaporated in vacuo to an oil, which was triturated 3× with hexane (100 mL) and dissolved in ACN (100 mL); Fmoc-Arg(PMC)-OH (6.63 g, 10 mm) and HOBT (1.53 g, 10 mm) were added, followed by DCC (4.1 g, 20 mm) and solution was stirred at RT. The urea by-product was filtered and the filtrate was evaporated in vacuo to an oil, which was triturated 3× with hexane (100 mL). The crude product was stirred in ACN (100 mL) and DEA (5 mL) was added and stirred at RT for 1 hr. The solution was evaporated in vacuo to an oil, which was triturated 3× with hexane (100 mL) to a solid. This dipeptide was combined in ACN (100 mL) with Fmoc-Cha-OH (3.93 g, 10 mm) and HOBT (1.53 g, 10 mm) and then DIC (2.52 g, 20 mm) was added and reaction stirred at RT for 16 hr. Solid tripeptide was filtered; tripeptide may also be recovered from the filtrate via evaporation and silica gel column chromatography. The tripeptide (5.0 g, 5 mm) was stirred in ACN (100 mL) containing DEA (5 mL) until deprotection is complete and then evaporated in vacuo and triturated with hexane 3× (100 mL). This was combined in ACN (100 mL) and 5-bromonicotinic acid (1.01 g, 5 mm) and HOBT (0.76 g, 5 mm) were added in, followed by DIC (1.26 g, 10 mm) and stirred at RT for 16 hr. The solution was evaporated in vacuo and purified via silica gel column chromatography. This protected product was then stirred with DCM/TFA (1:1; 50 mL) for 1 hr and then evaporated in vacuo to an oil, which was triturated 3× with Et$_2$O (100 mL) to afford white solid 3 as a triflouroacetate salt: MS m/e 657.4/659.4 (MH$^+$). $^1$H NMR (DMSO) 9.0 (s, 1H), 8.9 (s, 1H), 8.8 (d, 1H), 8.5 (s, 1H), 8.2 (d, 1H), 7.8 (d, 1H), 7.4 (s, 2H), 7.1–7.3 (m, 6H), 4.5 (m, 2H), 4.2 (q, 1H), 4.0 (s, 1H), 3.0 (m, 1H), 2.8 (q, 1H), 1.3–1.8 (m, 12H), 1.1 (m, 4H), 0.9 (m, 3H).

EXAMPLE 3

As a specific embodiment of an oral composition, 100 mg of the compound 1 of Example 1 is formulated with sufficient finely divided lactose to provide a total amount of 580 to 590 mg to fill a size O hard gel capsule.
Biology The compounds of the present invention modulate platelet activation induced by thrombin's proteolytic cleavage of its platelet surface receptor, and thereby activate/inhibit platelet aggregation. Compounds that exhibit agonist activity may be expected to aid in wound healing and tissue repair, while antagonist compounds may be useful in treating platelet-mediated thrombotic disorders such as arterial and venous thrombosis, acute myocardial infarction, reocclusion following thrombolytic therapy and angioplasty, and a variety of vaso-occlusive disorders.

EXAMPLE 4

In Vitro Thrombin Receptor Binding Assay

CHRF membranes (Jones, *Biochim. Biophys. Acta* 1992, 1136, 272) are thawed from −70° C., centrifuged at maximum speed for 5 min, washed twice with binding buffer (50 mM HEPES containing 5 mM MgCl$_2$ and 0.1% BSA), and re-suspended in binding buffer (25 mg/100 mL). 100 µl membranes are added to the 24-Wallac plates and delivered to the Tomtech apparatus. In a typical experiment, 6 µl of samples (from a 125 µg/mL intermediary plate, 20% DMSO) and 44 µl buffer are delivered to the plates (final conc. of compounds is 3.7 µg/mL, 0.6% DMSO). Similarly, 6 µl 20% DMSO and 44 µl buffer are delivered to both column 1 (NSB) and column 12 (TB). 10 µl Ser-pFPhe-Har-Leu-Har-Lys-Tyr-NH$_2$, SEQ. ID. No. 2 (721-40; 500 µM in deionized water) is added to column 1. 50 µl tritiated 721-40 (specific activity 46 Ci/mmol) is added to all the wells. The plates are mixed well for 20 seconds, incubated for 30 min, and then harvested with 10 mM HEPES/138 mM NaCl using the Skatron harvester. The filters (GF/C Brandel FPXLR 296 filters are presoaked 3 h in 0.5% polyethylenimine in HEPES/0.1 M N-acetylglucosamine) are set in saran wrap and dried for 3 min in the microwave, and placed in sample bags (Wallac 1450-432). 4.5 mL scintillation fluid (Wallac, Betaplate Scint 1205-440) is added. The bags are sealed, placed in filter cassettes (Wallac 1450-104), and analyzed on the microbeta counter.

EXAMPLE 5

In Vitro Agonist Platelet Aggregation Assay/Inhibition of Thrombin-Induced Gel-Filtered Platelet Aggregation Assay The percentage of platelet aggregation is calculated as an increase in light transmission of compound-treated platelet concentrate vs. control-treated platelet concentrate. Human blood is obtained from drug free, normal donors into tubes containing 0.13 M sodium citrate. Platelet rich plasma (PRP) is collected by centrifugation of whole blood at 200×g for 10 min at 25° C. The PRP (5 mL) is gel filtered through Sepharose 2B (bed volume 50 mL), and the platelet count is adjusted to 2×10$^7$ platelets per sample. The following constituents are added to a siliconized cuvette: concentrated platelet filtrate and Tyrode's buffer (0.14 M NaCl, 0.0027 M KCl, 0.012 M NaHCO$_3$, 0.76 mM Na$_2$HPO4, 0.0055 M glucose, 2 mg/mL BSA and 5.0 mM HEPES @ pH 7.4) in an amount equal to 350 l, 50 l of 20 mM calcium and 50 l of the test compound. Aggregation is monitored in a BIO-DATA aggregometer for the 3 min following the addition of agonist (thrombin 50 l of 1 unit/mL).

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:

1. A compound represented by the general formula (I):

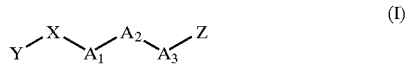

(I)

wherein $A_1$ is an amino acid residue selected from the group consisting of cyclohexylalanine, Leu, Ile, Arg, Lys, Phe, substituted Phe, Tyr and Trp;

$A_2$ is an amino acid residue selected from the group consisting of Lys, Orn, Arg, and homo Arg;

$A_3$ is an amino acid residue selected from the group consisting of Phe, substituted Phe, homo Phe, Tyr, Trp, phenylglycine, 2-thienylalanine, 3-thienylalanine, cyclohexylalanine, Leu, Ile, Asn, Gln, Arg, homo Arg, Orn and Lys;

X is selected from the group consisting of CO, CS, and $SO_2$;

Y is selected from the group consisting of aryl, substituted aryl, heterocycloalkyl, substituted heterocycloalkyl, heteroaryl, substituted heteroaryl, heteroarylethylenyl, substituted heteroarylethylenyl, arylacrylamidoheteroaryl, substituted arylacrylamidoheteroaryl, heteroarylacrylamidoheteroaryl and substituted heteroarylacrylamidoheteroaryl, provided that Y is not pyrrolidinyl, phenyl or 2-aminophenyl;

Z is selected from the group consisting of $NH_2$, NH-alkyl, NH-aralkyl, and Arg-$NH_2$; and wherein all amino acids are of the L configuration;

and any pharmaceutically acceptable salt thereof.

2. The compound of claim 1, wherein $A_3$ is an amino acid residue selected from the group consisting of Phe, substituted Phe, Tyr, Trp, phenylglycine, 2-thienylalanine, 3-thienylalanine, cyclohexylalanine, Leu Ile, Asn Gln, Arg, homo Arg, Orn and Lys; and Y is selected from the group consisting of heteroaryl, substituted heteroaryl, arylacrylamidoheteroaryl, and substituted arylacrylamidoheteroaryl;

and any pharmaceutically acceptable salt thereof.

3. The compound of claim 2, wherein $A_1$ is an amino acid residue selected from the group consisting of cyclohexylalanine, Leu, Ile, Phe, substituted Phe, Tyr and Trp;

$A_2$ is an amino acid residue selected from the group consisting of Lys and Arg;

$A_3$ is an amino acid residue selected from the group consisting of Phe, substituted Phe, Tyr, Trp, phenylglycine and 2-thienylalanine;

X is selected from the group consisting of CO and $SO_2$;

and any pharmaceutically acceptable salt thereof.

4. The compound of claim 3, wherein

X is CO;

Y is selected from the group consisting of benzothiophenyl, substituted benzothiophenyl, pyridinyl, substituted pyridinyl, triazolyl, substituted triazolyl, chromonyl, quinoxalinyl, thiadiazolyl, substituted thiadiazolyl, pyrazinyl, substituted pyrazinyl, pyridylethylenyl, substituted pyridylethylenyl, cinnamamido-triazolyl, substituted cinnamamido-triazolyl, thiophenylacrylamido-triazolyl and naphthylacrylamido-triazolyl;

Z is selected from the group consisting of $NH_2$ and Arg-$NH_2$;

and any pharmaceutically acceptable salt thereof.

5. The compound of claim 4, wherein $A_1$ is selected from the group consisting of Cha and Phe;

$A_2$ is selected from the group consisting of Arg and Lys;

$A_3$ is Phe;

and any pharmaceutically acceptable salt thereof.

6. The compound of claim 5, selected from the group consisting of:

(5-Bromopyridin-3-yl)carbonyl-cyclohexylalanyl-arginyl-phenylalanineamide;

2-Chromonylcarbonyl-cyclohexylalanyl-arginyl-phenylalanineamide;

(5-Aminotriazol-3-yl)carbonyl-cyclohexylalanyl-arginyl-phenylalanineamide;

[5-(χ-Methyl)cinnamamidotriazol-3-yl]carbonyl-cyclohexylalanyl-arginyl-phenylalanineamide;

{5-[3-(1-Naphthyl)acrylamido]triazol-3-yl}carbonyl-cyclohexylalanyl-arginyl-phenylalanineamide;

[Quinoxalin-2-yl]carbonyl-cyclohexylalanyl-arginyl-phenylalanineamide;

[5-(o-Chlorocinnamamido)triazol-3-yl]carbonyl-cyclohexylalanyl-arginyl-phenylalanineamide;

(6-Aminopyridin-3-yl)carbonyl-cyclohexylalanyl-arginyl-phenylalanineamide;

(5-Aminotriazol-3-yl)carbonyl-phenylalanyl-arginyl-phenylalanyl-arginineamide;

(5-Aminotriazol-3-yl)carbonyl-cyclohexylalanyl-lysinyl-phenylalanineamide;

{5-[3-(2-Thienyl)acrylamido]triazol-3-yl}carbonyl-cyclohexylalanyl-arginyl-phenylalanineamide;

[5-cinnamamidotriazol-3-yl]carbonyl-cyclohexylalanyl-arginyl-phenylalanineamide;
(6-Cinnamamidopyridin-3-yl)carbonyl-cyclohexylalanyl-arginyl-phenylalanineamide; or
(5-Chloro-3-methyl-benzothiophen-2-yl)carbonyl-cyclohexylalanyl-arginyl-phenylalanineamide;

and any pharmaceutically acceptable salt thereof.

7. A composition comprising a pharmaceutically acceptable carrier and a compound of claim 1.

8. A composition comprising a compound of claim 1 and a pharmaceutically acceptable carrier, wherein said composition is prepared by a process comprising:

a) mixing a compound of claim 1 and a pharmaceutically acceptable carrier; and b) recovering the composition of step (a).

9. A process for preparing a composition that contains a compound according to claim 1 in combination with a pharmaceutically acceptable carrier, said process comprising a) mixing a compound of claim 1 and a pharmaceutically acceptable carrier; and b) recovering the composition of step (a).

* * * * *

SEQUENCE LISTING

```
<160> NUMBER OF SEQ ID NOS: 2

<210> SEQ ID NO 1
<211> LENGTH: 6
<212> TYPE: PRT
<213> ORGANISM: Homo sapiens

<400> SEQUENCE: 1

Ser Phe Leu Leu Arg Asn
1               5

<210> SEQ ID NO 2
<211> LENGTH: 7
<212> TYPE: PRT
<213> ORGANISM: Artificial
<220> FEATURE:
<223> OTHER INFORMATION: Sequence is an artificial peptide antagonist
      for PAR1 receptor
<220> FEATURE:
```

-continued

```
<221> NAME/KEY: MISC_FEATURE
<222> LOCATION: (2)..(2)
<223> OTHER INFORMATION: X is para-fluoro-phenylalanine
<220> FEATURE:
<221> NAME/KEY: MISC_FEATURE
<222> LOCATION: (3)..(3)
<223> OTHER INFORMATION: X is homoarginine
<220> FEATURE:
<221> NAME/KEY: MISC_FEATURE
<222> LOCATION: (5)..(5)
<223> OTHER INFORMATION: X is homoarginine

<400> SEQUENCE: 2

Ser Xaa Xaa Leu Xaa Lys Tyr
1               5
```